United States Patent [19]

Flemer, III

[11] Plant 4,632

[45] Jan. 27, 1981

[54] FLOWERING CRAB APPLE TREE

[75] Inventor: William Flemer, III, Princeton, N.J.

[73] Assignee: Treesearch, Kingston, N.J.

[21] Appl. No.: 6,508

[22] Filed: Jan. 25, 1979

[51] Int. Cl.[3] ..... A01H 5/03

[52] U.S. Cl. ..... Plt./34

[58] Field of Search ..... Plt./34

*Primary Examiner*—Robert E. Bagwill

*Attorney, Agent, or Firm*—Frank B. Robb

[57] ABSTRACT

There is disclosed a new variety of *Malus hupehensis* which produces abundance of flowers having strong purplish pink appearance on a tree in bloom, dark red young leaves, becoming dark green when mature, with high resistance to apple scab fungus and fire blight.

2 Drawing Figures

My present invention relates to a new and distinct variety of flowering crab apple tree which was discovered by me in a row of hybrid seedlings of *Malus hupehensis* crossed with *Malus atrosanguinea,* none of which species is a patented variety.

I was first attracted to this variety which is one of many grown in the nursery on the property owned by Princeton Nurseries in Plainsboro Township, N.J., and which are grown in my care and at my direction, the seedling being first attractive to me because of the colorful dark red young leaves, very abundant pink flowers with rose margins and leathery dark green mature foliage.

In selecting this particular seedling I have been careful to observe the same through the maturity of this seedling, having first propagated the same by bud-grafting at the nursery referred to herein.

As a result of this careful consideration and observation of the growth of the seedling hereof, it is apparent that it is distinguished from its parents as well as from all other crab apple varieties of which I am aware, as evidenced by the following unique combination of characteristics which are outstanding therein and make it distinct in its own way:

1. Very abundant quantity of flowers;
2. Deep purplish pink of the flowers as they appear when they begin to open, with the pink overall appearance of the blooms when fully open;
3. The dark red young leaves and leathery dark green mature foliage ultimately present on the tree;
4. The high resistance to apple scab fungus (*Venturia inaequalis*) and fire blight (*Erwinia amylovora*) when compared to other crab apple varieties grown in adjacent rows.

I have effected asexually reproduction of my new variety, which I have chosen to designate as "Strawberry Parfait" because of its rather bi-color effect, and as performed by me, by bud-grafting in Plainsboro Township, N.J., which establishes that the foregoing characteristics and distinctions come true to form and are established and transmitted through succeeding propagations.

In the accompanying drawing, I have shown at the upper portion thereof a cluster of flowers which are probably representative of the general individual appearance, the flowers passing through color stages of deep purplish pink as the flowers begin to open, to moderate pink for fully opened flowers as depicted in color as nearly true as it is reasonably possible to make the same in a color illustration of this character.

The following is a detailed description of my new variety, with color terminology in accordance with the Munsell Color Chart, published by Munsell Color Company, Inc. and denominated Nickerson Color Fan, except where general color terms of ordinary dictionary significance are applicable and according to my personal observations and judgment in the use of such color designations and the color chart associated therewith:

Parentage: Seedling.

*Seed parent.*—*Malus hupehensis* (A Tea crab apple sometimes known as a Rose crab apple).

*Pollen parent.*—*Malus atrosanguinea,* or Carmine Crab Apple which was originally a clon from Japan.

Propagation: Holds its distinguishing characteristics through succeeding propagations by bud-grafting.

Locality where grown and observed: Plainsboro Township, N.J.

Tree: Medium size; spreading; vase-shaped; tall; hardy.

*Trunk.*—Slender; rough.

*Branches.*—Slender; smooth. Lenticels — Not abundant. Color — Grayish brown 7.5 YR 3/2. Number — Two per cm. of length.

Foliage:

*Leaves.*—Moderately abundant, very thick and leathery. Size — Length — About 10 cm. Width — Five to six cm. Shape — Ovate acuminate. Color — When expanding, dark red 5R 3/7. Mature leaves, Upper surface — Grayish Olive Green 5 GY 3/2. Lower surface — Moderate olive green 7.5 GY 4/4. Margin — Minutely serrate. Petiole — Medium length (about three cm. long). Glands — None. Stipules — Paired 1.2 cm. long.

Flower buds: Very hardy.

*Size.*—0.3 cm. long.

*Shape.*—Ovate; pointed.

*Color.*—Moderate reddish brown 10R 3/4.

Flowers:

*Blooming season.*—First bloom — About April 20 in Central New Jersey. Full bloom — About April 27 in normal years in Central New Jersey.

*Quantity.*—Abundant.

*Size.*—Large.

*Petalage.*—Number of petals — Five. Shape of petals — Widely ovate. Size of petals — Length — About 2 cm. Width — About 1.5 cm. Color — As the flowers open they appear as a deep purplish pink changing to moderate pink (2.5R 8/5) when fully open.

Fruits:

*Borne.*—Fall. *Quantity.*—Abundant.

*Size.*—About 1.2 cm. in diameter; round.

*Color.*—Green yellow with dull red cheek; strong red 5R 4/12.

I claim:

1. A new and distinct variety of flowering crab apple tree substantially as herein shown and described, characterized particularly as to novelty by the unique combination of the very abundant quantity of blooms which are deep purplish pink as the blooms open, becoming moderate pink when fully open, dark red young leaves which become leathery dark green at maturity, and very high resistance to scab fungus (*Venturia inaequalis*) and fire blight (*Erwinia amylovora*).

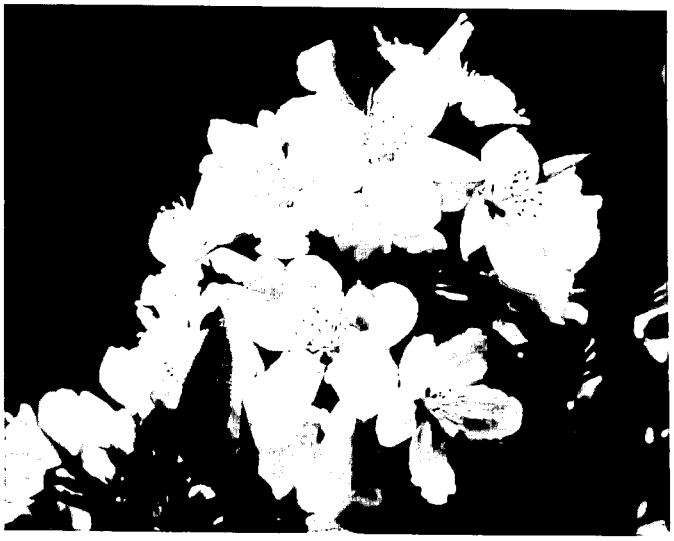
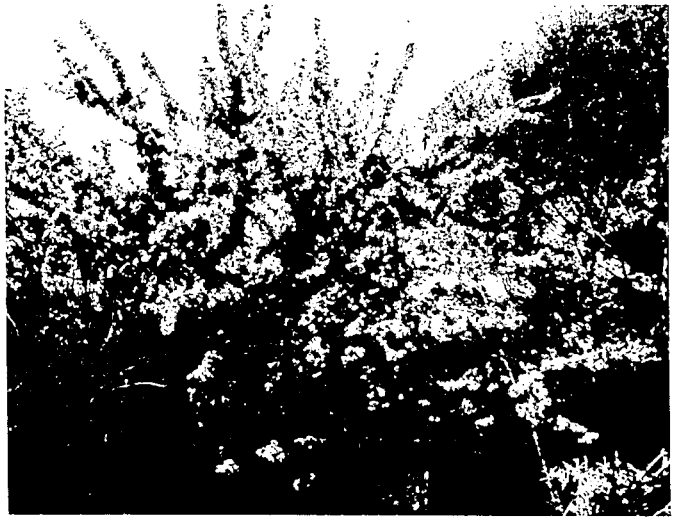

* * * * *